United States Patent
Nevler et al.

(10) Patent No.: US 9,839,584 B2
(45) Date of Patent: *Dec. 12, 2017

(54) NASOGASTRIC TUBE

(75) Inventors: Avinoam Nevler, Reut (IL); Orit Shaked, Ramat Yishai (IL); Eyal Haytman, Kfar Vradim (IL)

(73) Assignee: NUTRISEAL LIMITED PARTNERSHIP, Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/982,289

(22) PCT Filed: Jul. 16, 2012

(86) PCT No.: PCT/US2012/046850
§ 371 (c)(1),
(2), (4) Date: Jul. 29, 2013

(87) PCT Pub. No.: WO2013/012774
PCT Pub. Date: Jan. 24, 2013

(65) Prior Publication Data
US 2013/0310806 A1 Nov. 21, 2013

Related U.S. Application Data

(60) Provisional application No. 61/508,670, filed on Jul. 17, 2011.

(51) Int. Cl.
*A61J 15/00* (2006.01)
(52) U.S. Cl.
CPC ......... *A61J 15/0003* (2013.01); *A61J 15/003* (2013.01); *A61J 15/0073* (2013.01)

(58) Field of Classification Search
CPC ...... A61B 17/3478; A61B 2017/00269; A61B 2017/306; A61F 2/04; A61F 5/0069;
(Continued)

(56) References Cited

U.S. PATENT DOCUMENTS 5,389,074 A    2/1995  Parker et al.
5,707,351 A *  1/1998  Dorsey, III ......... A61M 1/0062
                                                604/30
(Continued)

FOREIGN PATENT DOCUMENTS

EP    2301512 A2 *  3/2011  ............ A61J 15/003
WO    2003034976     5/2013
WO    2015198297    12/2015

OTHER PUBLICATIONS

International Search Report from a foreign patent office in a counterpart foreign application, dated Nov. 20, 2012, two pages.

*Primary Examiner* — Bhisma Mehta
*Assistant Examiner* — William Frehe
(74) *Attorney, Agent, or Firm* — Roy Gross; The Roy Gross Law Firm, LLC

(57) ABSTRACT

A nasogastric tube (10) including a main lumen (12) having one or more proximal connectors (14) for connecting to a source of substances or pressure, and one or more vacuum lumens (16) peripherally surrounding the main lumen (12), each vacuum lumen (16) including a vacuum sealing portion (24), which includes one or more suction ports (26) for sealingly drawing an inner wall of an esophagus thereagainst.

16 Claims, 2 Drawing Sheets

(58) Field of Classification Search
CPC ............... A61M 39/22; A61M 39/223; A61M 2039/224; A61J 15/003; A61J 15/0003
USPC ............................... 604/911, 43, 93.01, 334
See application file for complete search history.

(56) References Cited

U.S. PATENT DOCUMENTS

| | | | |
|---|---|---|---|
| 6,695,764 B2* | 2/2004 | Silverman | A61F 2/04 600/29 |
| 8,100,874 B1 | 1/2012 | Jordan et al. | |
| 2003/0208209 A1* | 11/2003 | Gambale et al. | 606/144 |
| 2004/0153098 A1* | 8/2004 | Chin | A61B 17/00008 606/129 |
| 2004/0220515 A1* | 11/2004 | Constantz | A61M 25/0032 604/43 |
| 2005/0059962 A1* | 3/2005 | Phan | A61B 18/1492 606/41 |
| 2009/0306626 A1 | 12/2009 | Sinha et al. | |
| 2011/0046653 A1* | 2/2011 | Addington | A61B 5/04882 606/196 |
| 2013/0310806 A1 | 11/2013 | Nevler et al. | |
| 2014/0188080 A1 | 7/2014 | Besser et al. | |

\* cited by examiner

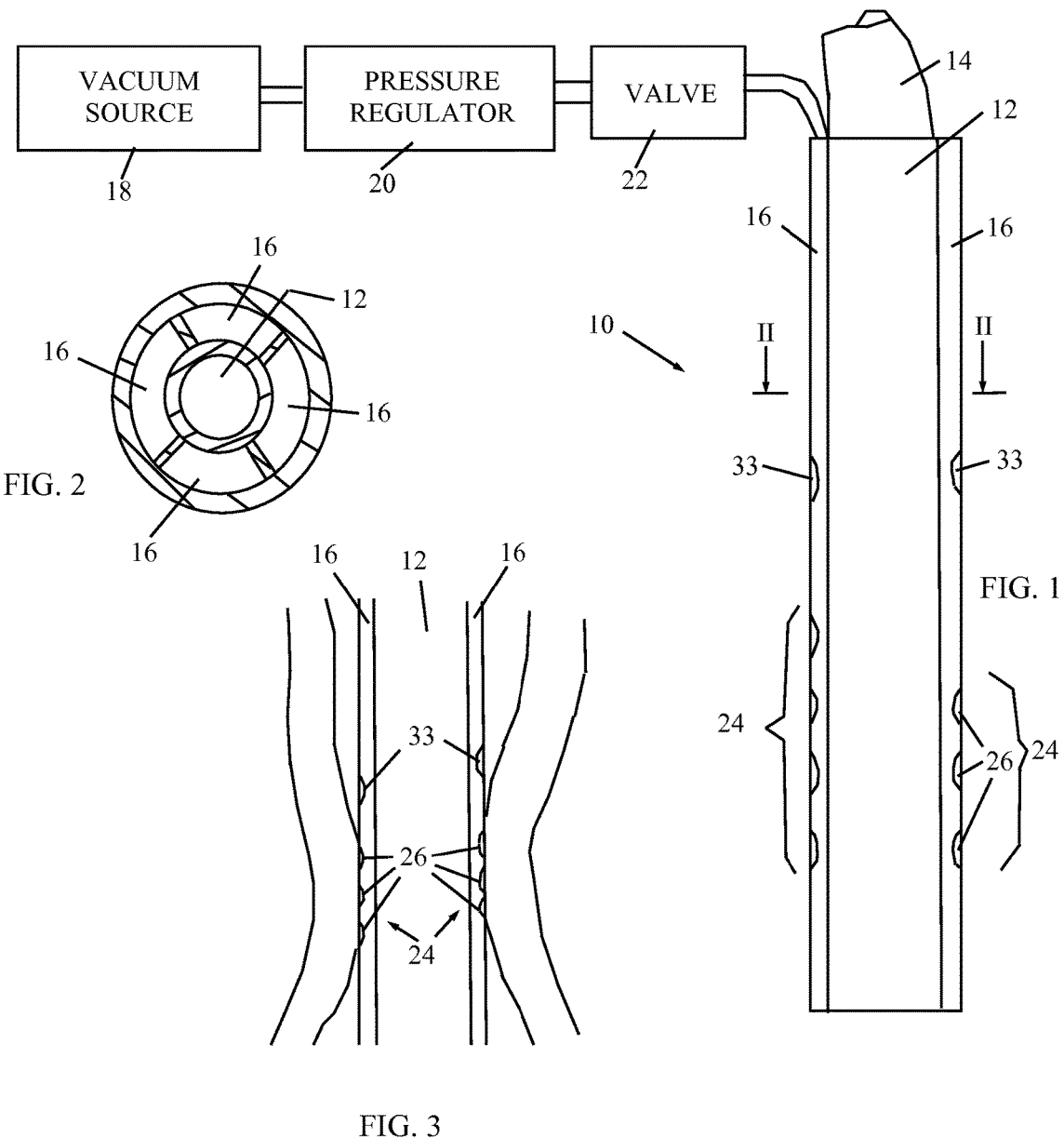

NASOGASTRIC TUBE

FIELD OF THE INVENTION

The present invention relates generally to nasogastric tubes.

BACKGROUND OF THE INVENTION

Enteral feeding is a form of hyperalimentation and metabolic support in which nutrient formulas or medicaments are delivered directly to the GI tract, either to the stomach or the duodenum. A nasogastric tube (NGT) is used for feeding and administering drugs and other oral agents. The tube is inserted into the patient's esophagus and stomach in order to ensure the passage of the agents into the stomach and not into the lungs. The NGT can also be used for sucking fluids from the stomach.

However, the use of NGTs can have disadvantages. Minor complications include nose bleeds, sinusitis, and a sore throat. Sometimes more significant complications occur including erosion of the nose where the tube is anchored, esophageal perforation, pulmonary aspiration, a collapsed lung, or intracranial placement of the tube.

Even worse, during feeding, excessive gastric pressure may result. From time to time, the body relieves such excess gastric pressure by expelling gas or liquid or reflux fluid. The fluids are expelled from the stomach through the esophagus to the mouth or nasal pathways. The reflux fluids may be inhaled into the lungs with possible risk of aspiration pneumonia, bacterial infection in the pharynx or esophagus or any other ailments. Accordingly, numerous studies have linked the use of the NGT to an increase in ventilator-associated pneumonia (VAP). VAP is the most common nosocomial infection in the intensive care unit (ICU), and it is associated with prolonged hospitalization, increased health care costs, and high attributable mortality.

There thus exists a pressing need for an NGT that is capable of significantly reducing the risk of reflux food and developing VAP.

SUMMARY OF THE INVENTION

The present invention seeks to provide a novel nasogastric tube, as is described more in detail hereinbelow. The NGT includes a tube and a vacuum control unit. The vacuum control unit couples the esophagus to the tube thus disabling the reflux of the food along the esophagus to the trachea. The NGT can be used in ICU, or elsewhere, in order to reduce the complications associated with reflux such as the risk of VAP.

The present invention overcomes the problems associated with prior art NGTs by sealing between the NGT and the inner wall of the esophagus. In a preferred embodiment, the inner wall of the esophagus is drawn by negative pressure (vacuum) towards and against the outer contour of the NGT. A vacuum control unit, which is connected to the hospital vacuum unit or any other vacuum unit, enables either simultaneous vacuum pressure in one or more suction units of the NGT or changeable vacuum pressure between the different suction units. In this way, the NGT of the present invention prevents reflux and aspiration of substances or liquids into the patient's lungs, while obviating the need to remove and replace the entire device from the patient's esophagus.

In another embodiment, the NGT of the present invention may be used in other places in the GI tract.

There is provided in accordance with an embodiment of the present invention a nasogastric tube including a main lumen having one or more proximal connectors for connecting to a source of substances (such as for feeding food or introducing drugs or other substances) or pressure, and one or more vacuum lumens peripherally surrounding the main lumen, each vacuum lumen including a vacuum sealing portion, which includes one or more suction ports for sealingly drawing an inner wall of an esophagus thereagainst.

In accordance with an embodiment of the present invention a vacuum source is connected to the one or more vacuum lumens. Some of the vacuum lumens may have more suction ports than others of the vacuum lumens. The vacuum lumens may be connected to the vacuum source via a pressure regulator and a valve.

There is also provided in accordance with an embodiment of the present invention a method including introducing the nasogastric tube into an esophagus of a patient, and applying vacuum to the one or more suction ports so as to sealingly draw an inner wall of an esophagus thereagainst.

The method may further include regulating the vacuum so that a suction level is not constant over time in the vacuum sealing portions.

The method may further include suction of saliva or other oropharyngeal secretions via one or more suctions ports that are proximal to the vacuum sealing portion.

BRIEF DESCRIPTION OF THE DRAWINGS

The present invention will be understood and appreciated more fully from the following detailed description taken in conjunction with the drawings in which:

FIG. 1 is a simplified schematic illustration of a nasogastric tube, constructed and operative in accordance with a non-limiting embodiment of the present invention;

FIG. 2 is a simplified sectional illustration of the NGT of FIG. 1, taken along lines II-II in FIG. 1;

FIG. 3 is a simplified schematic illustration of the nasogastric tube being used to suck and seal the inner wall of the esophagus against the NGT, in accordance with an embodiment of the present invention.

DETAILED DESCRIPTION OF EMBODIMENTS

Figure 4:
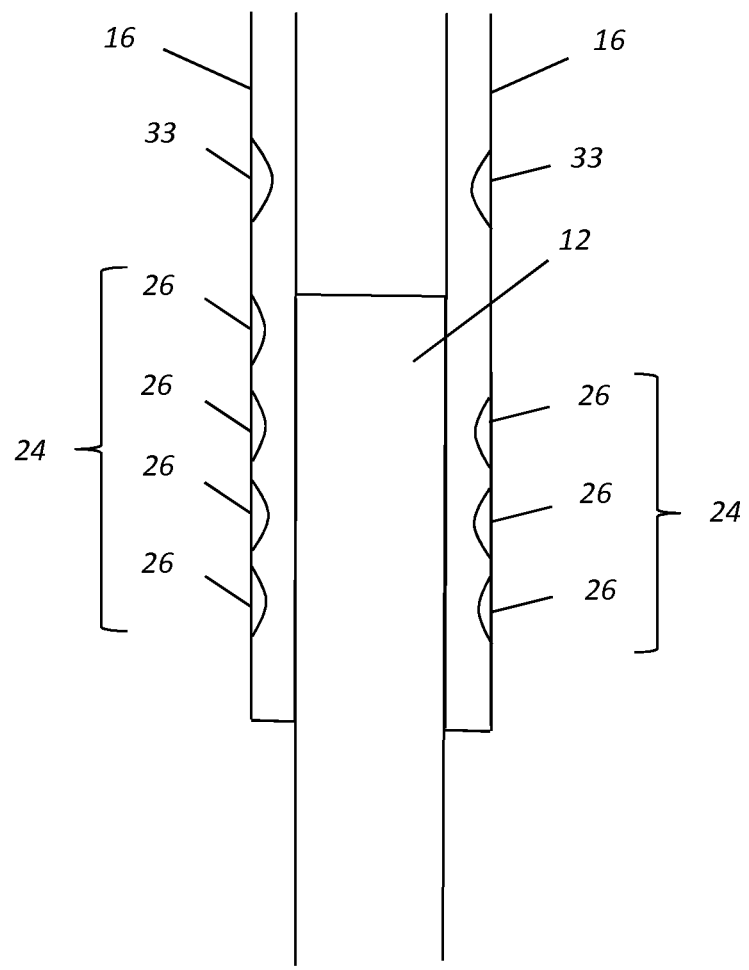
FIG. 4 is an illustration of the nasogastric tube of FIG. 1 having the vacuum lumens as a separate unit from the main lumen and which is slid over the main lumen.

Reference is now made to FIGS. 1 and 2, which illustrate a nasogastric tube 10, constructed and operative in accordance with a non-limiting embodiment of the present invention.

NGT 10 includes a main (typically, but not necessarily, central) lumen 12. Main lumen 12 may be used to feed and administer drugs and other oral agents, and may also be used for sucking fluids from the stomach. As such, as is known in the art, main lumen 12 may be a double lumen, one lumen for feeding and the other lumen for suction (not to be confused with the vacuum lumens mentioned later). Main lumen 12 is provided with one or more suitable proximal connectors 14 for connecting to a source of substances for feeding or administering, and optionally to a source of pressure (e.g., suction), as is known in the art.

NGT 10 includes one or more vacuum lumens 16 that peripherally surround main lumen 12. The term "peripherally surround" as used in the description and claims, encompasses continuous surrounding (no gaps between the vacuum lumens or one continuous, peripheral vacuum lumen) and discontinuous surrounding (wherein there are separations between discrete vacuum lumens), In one embodiment, illustrated in FIG. 2, there are four vacuum lumens 16 peripherally spaced around main lumen 12; the invention is not limited to this number of vacuum lumens. The vacuum lumens 16 may be equally or unequally spaced from each other. Main lumen 12 and vacuum lumens 16 are thus arranged as concentrically arranged conduits. Vacuum lumens 16 are connected to a vacuum source 18, such as via a pressure regulator 20 and a valve 22, which form a vacuum control unit.

Main lumen 12 may be constructed from any suitable biocompatible material, such as but not limited to, polyurethane, silicone, polyvinyl chloride and many others. The vacuum lumens 16 may be constructed of similar materials, but alternatively may be constructed of medically safe metals, such as but not limited to, stainless steel, titanium alloys, NITINOL and others. Generally, without limitation, main lumen 12 may have a length in the range of 50 to 130 cm, with an outside diameter in the range of 5-12 Fr.

The main lumen 12 and the vacuum lumens 16 may be constructed as one unit. Alternatively, vacuum lumens 16 may be a separate unit which is slid over main lumen 12, as illustrated at FIG. 4, after insertion of main lumen 12 into the patient. As another alternative, vacuum lumens 16 may be first introduced into the patient, and main lumen 12 may be slid through the vacuum lumens 16.

Each vacuum lumen 16 includes a vacuum sealing portion 24, which includes one or more suction ports 26. As seen in FIG. 1, some vacuum lumens 16 may have more suction ports than others. As seen in FIG. 3, upon application of vacuum from vacuum source 18, the inner wall of the esophagus is drawn by negative pressure towards and against suction ports 26 (the outer contour of NGT 10). The outer contour of NGT 10, at least at vacuum sealing portion 24, is preferably round (circular or oval), for better conforming to and sealing the esophagus. In one embodiment, the vacuum sealing restricts at least 60% of the passage through the esophagus.

Pressure regulator 20 may be used to reduce or otherwise regulate the negative pressure from vacuum source 18. For example, pressure regulator 20 may be used to match the vacuum level from vacuum source 18 to the vacuum level needed in vacuum sealing portion 24. The valve 22 may be used to shift the vacuum between the different vacuum lumens 16 so that the suction level is not constant over time in the vacuum sealing portion 24, which may provide variability in how the esophagus wall is sucked in, and for how long.

NGT 10 may be provided with different numbers of vacuum sealing portions 24 and suction ports 26, and the vacuum to the sealing portions 24 may be regulated so as to create peristaltic movement or other oscillatory movement of the esophagus.

In accordance with an embodiment of the invention, one or more auxiliary suction ports 33 are provided proximal to vacuum sealing portion 24. Since vacuum sealing portion 24 seals off the esophagus, any oropharyngeal secretions, such as saliva, may accumulate above (i.e., proximal to) vacuum sealing portion 24. Auxiliary suction ports 33 may be used to suck and remove such secretions, Vacuum source 18 is preferably activated following the insertion and localization of NGT 10 in the esophagus in order to reduce the risk of VAP, or other bacterial infections, by preventing or minimizing reflux food and liquid aspiration into the lungs.

One method of using NGT 10 of the present invention includes the following steps, without limitation and not necessarily in sequential order:

a) introducing NGT 10 into the esophagus of the subject;
b) applying vacuum to the vacuum sealing portion(s) 24;
c) adjusting the vacuum level (which may be done before step a); and
d) after achieving a desired sealing of the esophagus wall to NGT 10, changing the vacuum intervals between the vacuum lumens 16, manually or automatically, such that NGT 10 remains intact to the esophagus.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A system for supplying substances or pressure to the stomach and/or duodenum, through the esophagus, while sealing the esophagus against reflux, comprising: a tube comprising: a main lumen having one or more proximal connectors connectable to a source of substances or pressure, and a distal end configured to be positioned within the stomach and/or duodenum when in use, the distal end comprising an opening that during use allows access to the stomach and/or duodenum for the substances or pressure, and at least four vacuum lumens circumferentially surrounding said main lumen, each said at least four vacuum lumens comprising a vacuum sealing portion; wherein a distance between said opening and said vacuum sealing portions is such that when said distal end is positioned within the stomach and/or duodenum, said vacuum sealing portion is located within the esophagus; and wherein said distance is fixed; and wherein each said vacuum sealing portion comprises one or more suction ports; said one or more suction ports positioned along a longitudinal axis of said vacuum lumen and configured to circumferentially and sealingly draw an inner wall of the esophagus thereagainst; and a valve connected to said at least four vacuum lumens, said valve configured to shift an applied vacuum between different ones of said at least four vacuum lumens, thereby: a) varying how said inner wall of the esophagus is circumferentially and sealingly drawn, and b) changing a vacuum interval between said different ones of said at least four vacuum lumens.

2. The system according to claim 1, further comprising a vacuum source connected to said at least four vacuum lumens.

3. The system according to claim 2, further comprising a pressure regulator which connects said at least four vacuum lumens to said vacuum source.

4. The system according to claim 1, wherein each said vacuum sealing portion comprises at least two suction ports.

5. The system according to claim 4, wherein the at least two suction ports are configured to create peristaltic movement or other oscillatory movement of the esophagus.

6. The system according to claim 1, wherein some of said at least four vacuum lumens have more suction ports than others of said vacuum lumens.

7. The system according to claim 1, wherein said main lumen and said at least four vacuum lumens are constructed as one unit.

8. The system according to claim 1, wherein said at least four vacuum lumens are a separate unit from said main lumen and said at least four vacuum lumens and said main lumen are slidable relative to one another.

9. The system according to claim 1, wherein said main lumen and said at least four vacuum lumens are arranged as concentrically arranged conduits.

10. The system according to claim 1, further comprising one or more auxiliary suction ports proximal to said vacuum sealing portion.

11. The system according to claim 1, wherein the vacuum intervals are changed such that a vacuum level is not constant over time.

12. The system according to claim 1, wherein the tube is made from a biocompatible material.

13. The system according to claim 1, wherein the main lumen is made from polyurethane, silicone, or polyvinyl chloride and the at least four vacuum lumens are made from polyurethane, silicone, polyvinyl chloride, stainless steel, titanium alloys, or nitinol.

14. The system according to claim 1, wherein the main lumen has a length of 50 to 130 cm.

15. The system according to claim 1, wherein the main lumen has an outer diameter in the range of 5-12 Fr.

16. The system according to claim 1, wherein the vacuum sealing portions of said at least four vacuum lumens are round or oval.

* * * * *